(12) United States Patent
Wilson et al.

(10) Patent No.: US 10,813,761 B2
(45) Date of Patent: Oct. 27, 2020

(54) TETHERED IMPLANTABLE DEVICE HAVING A VORTICAL INTRACARDIAC VELOCITY ADJUSTING BALLOON

(71) Applicant: Harmony Development Group, Inc., Cornelius, NC (US)

(72) Inventors: John Wilson, Cornelius, NC (US); Christopher Seguin, Norton, MA (US)

(73) Assignee: Harmony Development Group, Inc., Cornelius, NC (US)

( * ) Notice: Subject to any disclaimer, the term of this patent is extended or adjusted under 35 U.S.C. 154(b) by 0 days.

(21) Appl. No.: 15/987,621

(22) Filed: May 23, 2018

(65) Prior Publication Data
US 2018/0338833 A1    Nov. 29, 2018

Related U.S. Application Data

(60) Provisional application No. 62/509,976, filed on May 23, 2017, provisional application No. 62/509,905, filed on May 23, 2017.

(51) Int. Cl.
*A61F 2/24* (2006.01)
*A61B 17/12* (2006.01)
(Continued)

(52) U.S. Cl.
CPC ...... *A61F 2/2487* (2013.01); *A61B 17/12122* (2013.01); *A61B 17/12136* (2013.01); *A61F 2/2412* (2013.01); *A61F 2/2433* (2013.01); *A61F 2/2442* (2013.01); *A61B 17/00234* (2013.01); *A61B 2017/00017* (2013.01); *A61B 2017/00022* (2013.01);
(Continued)

(58) Field of Classification Search
CPC .... A61F 2/2487; A61F 2/2412; A61F 2/2433; A61M 1/12; A61M 1/122; A61M 1/1037; A61M 1/1086
USPC .......................................................... 600/16
See application file for complete search history.

(56) References Cited

U.S. PATENT DOCUMENTS

6,406,422 B1 * 6/2002 Landesberg ........ A61M 1/1072
                                                             600/17
6,827,682 B2    12/2004 Bugge et al.
(Continued)

FOREIGN PATENT DOCUMENTS

CN          106214289 A       12/2016
WO     WO-2012/130052 A1     10/2012
(Continued)

OTHER PUBLICATIONS

International Search Report and Written Opinion for International Application No. PCT/US2018/035427 dated Jul. 27, 2018.
(Continued)

*Primary Examiner* — John R Downey
(74) *Attorney, Agent, or Firm* — Stephen J. Kenny; Robert Piston; Foley Hoag LLP

(57) ABSTRACT

An implant system for restoring and improving physiological intracardiac flow in a human heart is provided including an expandable balloon defining a fluid reservoir for positioning in a chamber of the human heart; a therapeutic apical base plate assembly attachable to the apex of the heart; and a tether assembly connected between the implant and the therapeutic apical base plate assembly.

19 Claims, 13 Drawing Sheets

(51) Int. Cl.
  *A61B 17/00* (2006.01)
  *A61B 17/34* (2006.01)
  *A61B 90/00* (2016.01)
  *A61F 2/06* (2013.01)
  *A61F 2/48* (2006.01)

(52) U.S. Cl.
  CPC ............ *A61B 2017/00221* (2013.01); *A61B 2017/00243* (2013.01); *A61B 2017/00539* (2013.01); *A61B 2017/00557* (2013.01); *A61B 2017/3425* (2013.01); *A61B 2090/036* (2016.02); *A61F 2002/068* (2013.01); *A61F 2002/482* (2013.01); *A61F 2002/485* (2013.01); *A61F 2210/009* (2013.01); *A61F 2220/0008* (2013.01); *A61F 2220/0033* (2013.01); *A61F 2220/0091* (2013.01); *A61F 2230/0013* (2013.01); *A61F 2250/0003* (2013.01); *A61F 2250/0013* (2013.01); *A61F 2250/0065* (2013.01); *A61F 2250/0069* (2013.01)

(56) References Cited

U.S. PATENT DOCUMENTS

| | | | |
|---|---|---|---|
| 7,435,257 B2 | 10/2008 | Lashinski et al. | |
| 7,854,762 B2 | 12/2010 | Speziali et al. | |
| 8,092,525 B2 | 1/2012 | Eliasen et al. | |
| 8,778,017 B2 | 7/2014 | Eliasen et al. | |
| 9,050,189 B2 | 6/2015 | Padala et al. | |
| 9,078,660 B2 | 7/2015 | Boutillette et al. | |
| 9,486,306 B2 | 11/2016 | Tegels et al. | |
| 9,498,330 B2 | 11/2016 | Solem | |
| 2003/0032855 A1 | 2/2003 | Shahinpoor | |
| 2006/0058871 A1 | 3/2006 | Zakay et al. | |
| 2006/0241745 A1* | 10/2006 | Solem | A61F 2/246 623/2.18 |
| 2007/0198082 A1 | 8/2007 | Kapadia et al. | |
| 2007/0265490 A1* | 11/2007 | Smith | A61M 1/1072 600/18 |
| 2007/0270943 A1 | 11/2007 | Solem et al. | |
| 2007/0282157 A1* | 12/2007 | Rottenberg | A61B 5/0215 600/16 |
| 2008/0064917 A1 | 3/2008 | Bar et al. | |
| 2008/0294251 A1* | 11/2008 | Annest | A61B 17/0401 623/3.1 |
| 2008/0306328 A1 | 12/2008 | Ercolani et al. | |
| 2009/0048668 A1 | 2/2009 | Wilson et al. | |
| 2009/0131849 A1 | 5/2009 | Maurer et al. | |
| 2009/0177028 A1 | 7/2009 | White | |
| 2009/0254195 A1* | 10/2009 | Khairkhahan | A61F 2/2487 623/23.67 |
| 2011/0022164 A1 | 1/2011 | Quinn et al. | |
| 2011/0196483 A1* | 8/2011 | Forsell | A61M 1/12 623/3.1 |
| 2011/0224655 A1 | 9/2011 | Asirvatham et al. | |
| 2013/0030519 A1* | 1/2013 | Tran | A61F 2/2433 623/2.11 |
| 2013/0172978 A1 | 7/2013 | Vidlund et al. | |
| 2013/0325110 A1 | 12/2013 | Khalil et al. | |
| 2014/0277404 A1* | 9/2014 | Wilson | A61F 2/2466 623/2.11 |
| 2014/0309732 A1* | 10/2014 | Solem | A61F 2/246 623/2.36 |
| 2014/0336751 A1 | 11/2014 | Kramer | |
| 2014/0371789 A1* | 12/2014 | Hariton | A61B 17/00234 606/215 |
| 2014/0371843 A1 | 12/2014 | Wilson et al. | |
| 2014/0371846 A1 | 12/2014 | Wilson et al. | |
| 2015/0073539 A1* | 3/2015 | Geiger | A61F 2/2439 623/2.11 |
| 2015/0112429 A1 | 4/2015 | Khairkhahan et al. | |
| 2015/0223934 A1* | 8/2015 | Vidlund | A61F 2/2457 623/2.11 |
| 2015/0245934 A1* | 9/2015 | Lombardi | A61F 2/2436 623/2.11 |
| 2016/0089234 A1 | 3/2016 | Gifford, III | |
| 2016/0089237 A1 | 3/2016 | Wilson et al. | |
| 2016/0113765 A1 | 4/2016 | Ganesan et al. | |
| 2016/0242909 A1 | 8/2016 | Ketai et al. | |
| 2016/0317290 A1* | 11/2016 | Chau | A61F 2/246 |
| 2017/0000935 A1 | 1/2017 | Vasilyev et al. | |
| 2017/0136162 A1* | 5/2017 | van Dort | A61M 1/1086 |
| 2017/0172737 A1 | 6/2017 | Kuetting et al. | |
| 2018/0015141 A1 | 1/2018 | Jay et al. | |
| 2018/0185145 A1 | 7/2018 | Wilson et al. | |
| 2018/0318071 A1 | 11/2018 | Lozonschi et al. | |
| 2018/0344461 A1 | 12/2018 | Wilson et al. | |

FOREIGN PATENT DOCUMENTS

| | | |
|---|---|---|
| WO | WO-2018/129312 A1 | 7/2018 |
| WO | WO-2018/129320 A1 | 7/2018 |
| WO | WO-2018/222894 A1 | 12/2018 |
| WO | WO-2019/006152 A1 | 1/2019 |
| WO | WO-2019/173385 A1 | 9/2019 |

OTHER PUBLICATIONS

International Search Report and Written Opinion for International Application No. PCT/US2018/034177 dated Jul. 20, 2018.
International Search Report and Written Opinion for International Application No. PCT/US2018/012586 dated Mar. 20, 2018.
International Search Report and Written Opinion for International Application No. PCT/US2018/034174 dated Jul. 27, 2018.
International Search Report and Written Opinion for International Application No. PCT/US2018/040066 dated Sep. 12, 2018.
International Search Report and Written Opinion for International Application No. PCT/US19/20816 dated Jul. 9, 2019.
International Search Report and Written Opinion for International Application No. PCT/US2018/12578 dated Mar. 28, 2018.

* cited by examiner

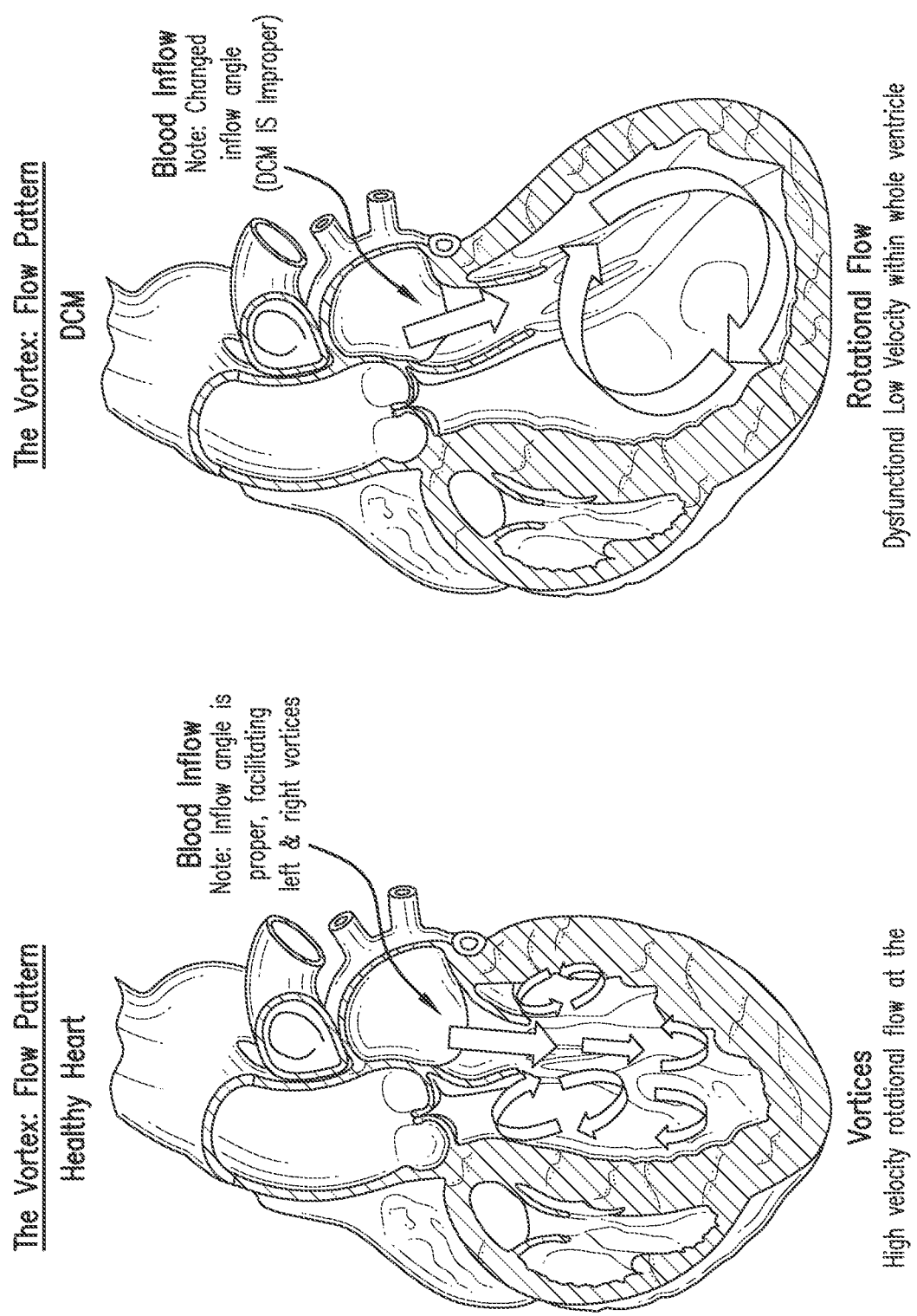

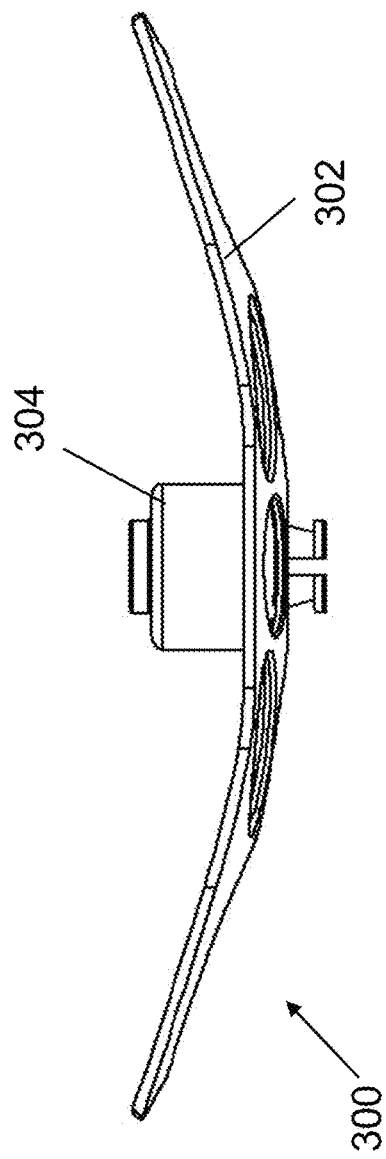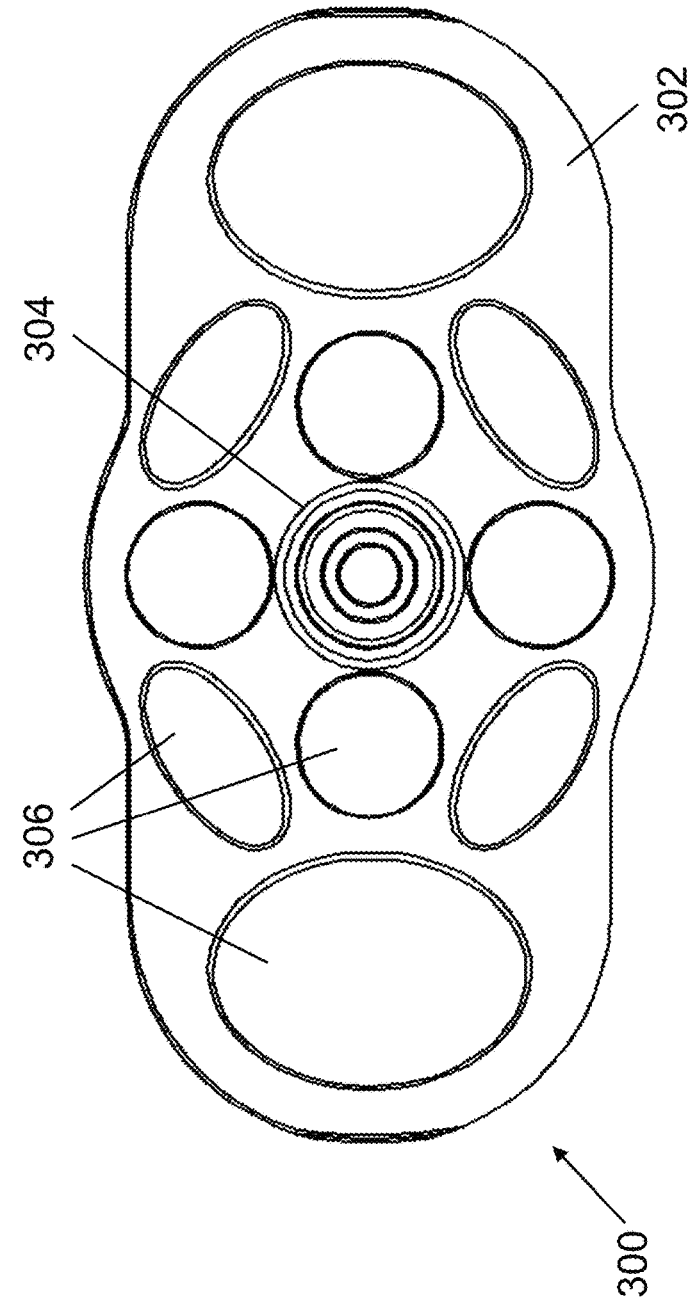

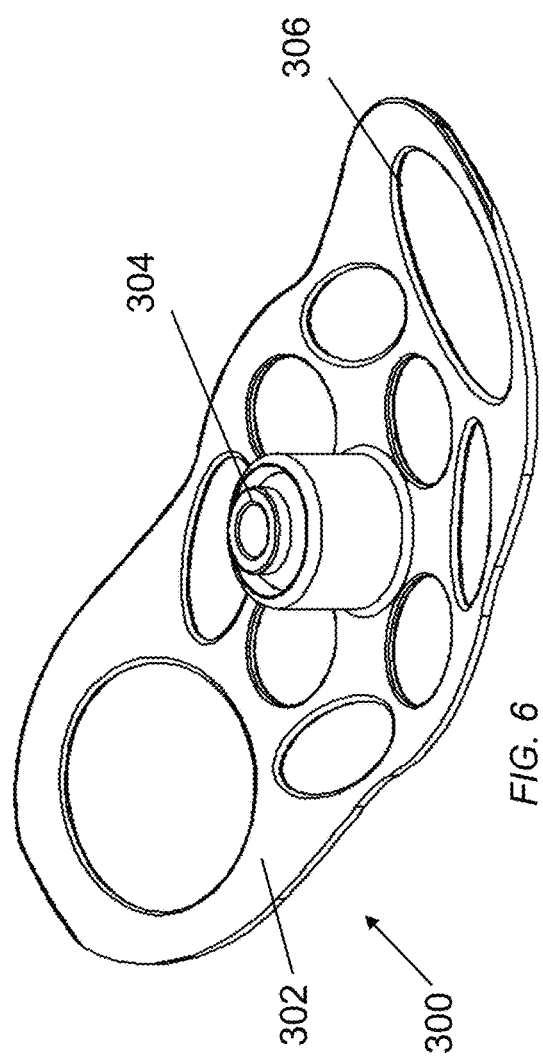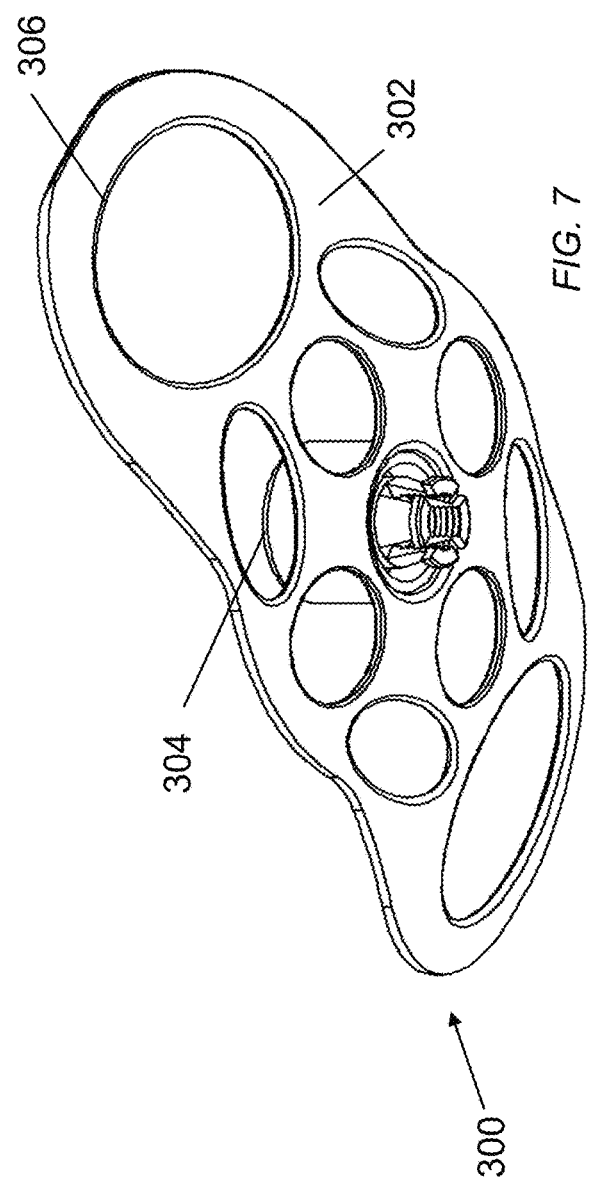
FIG. 6
FIG. 7

TETHERED IMPLANTABLE DEVICE HAVING A VORTICAL INTRACARDIAC VELOCITY ADJUSTING BALLOON

CROSS-REFERENCE TO RELATED APPLICATIONS

This application claims the benefit under 35 USC § 119(e) of U.S. Provisional Application Ser. Nos. 62/509,905 and 62/509,976 filed May 23, 2017, which are hereby incorporated by reference in its entirety.

TECHNICAL FIELD

The present disclosure relates generally to an implant within a human heart for restoring and improving physiologic intracardiac flow having a vortical intracardiac velocity adjusting balloon.

SUMMARY

An implant system for restoring and improving physiological intracardiac flow in a human heart is provided including an expandable balloon defining a fluid reservoir for positioning in the ventricle of the human heart; a therapeutic apical base plate assembly attachable to the apex of the heart; and a tether assembly connected between the implant and the therapeutic apical base plate assembly.

In some embodiments, the balloon is adjustable axially and latitudinally. In some embodiments, the balloon defines a concave shape, a convex shape, or another shape at the distal portion thereof. In some embodiments, the balloon includes a balloon within a balloon configuration. The balloon can be adjustable. The balloon can be asymmetric or symmetric.

In some embodiments, the balloon restores the intraventricular elliptical shape of a dysfunctional ventricle. The balloon defines a volume and includes an outer surface to firmly contact the ventricular endocardium.

In some embodiments, the balloon is shape compliant to form to any shape within the atrium, the ventricle, or other existing spaces to include the apical endocardium or the left atrial appendage.

In some embodiments, the balloon includes an outer material to promote endothelization and minimize thrombogenicity. The material can detachable from the balloon.

In some embodiments, the tether includes a rigid shaft. The balloon can be capable of moving the shaft and/or the shaft can be capable of moving the balloon.

In some embodiments, the fluid reservoirs are in external communication. The balloon can include a plurality of balloons, each disposed in a separate heart chambers, and being in fluid communication with each other. In some embodiments, the fluid reservoirs are in internal communication. The fluid in the reservoir is gas, liquid or gel.

In some embodiments, the implant system includes sensoring nodes, transducers, or other diagnostic surveillance equipment that transmit information to an external receiving platform.

In some embodiments, the implant system includes a sensoring and control module and/or a communications unit.

BRIEF DESCRIPTION OF THE DRAWINGS

The objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

FIG. 1 is a diagram illustrating the vortex flow pattern of a healthy human heart.

FIG. 2 is a diagram illustrating the dysfunctional vortex flow pattern of a human heart with pathology.

FIG. 4 is a side view of the therapeutic apical base plate assembly in accordance with exemplary embodiments of the disclosed subject matter.

FIG. 5 is top view of the therapeutic apical base plate assembly in accordance with exemplary embodiments of the disclosed subject matter.

FIGS. 6-7 are perspective views of the therapeutic apical base plate assembly in accordance with exemplary embodiments of the disclosed subject matter.

DETAILED DESCRIPTION

Figure 3:
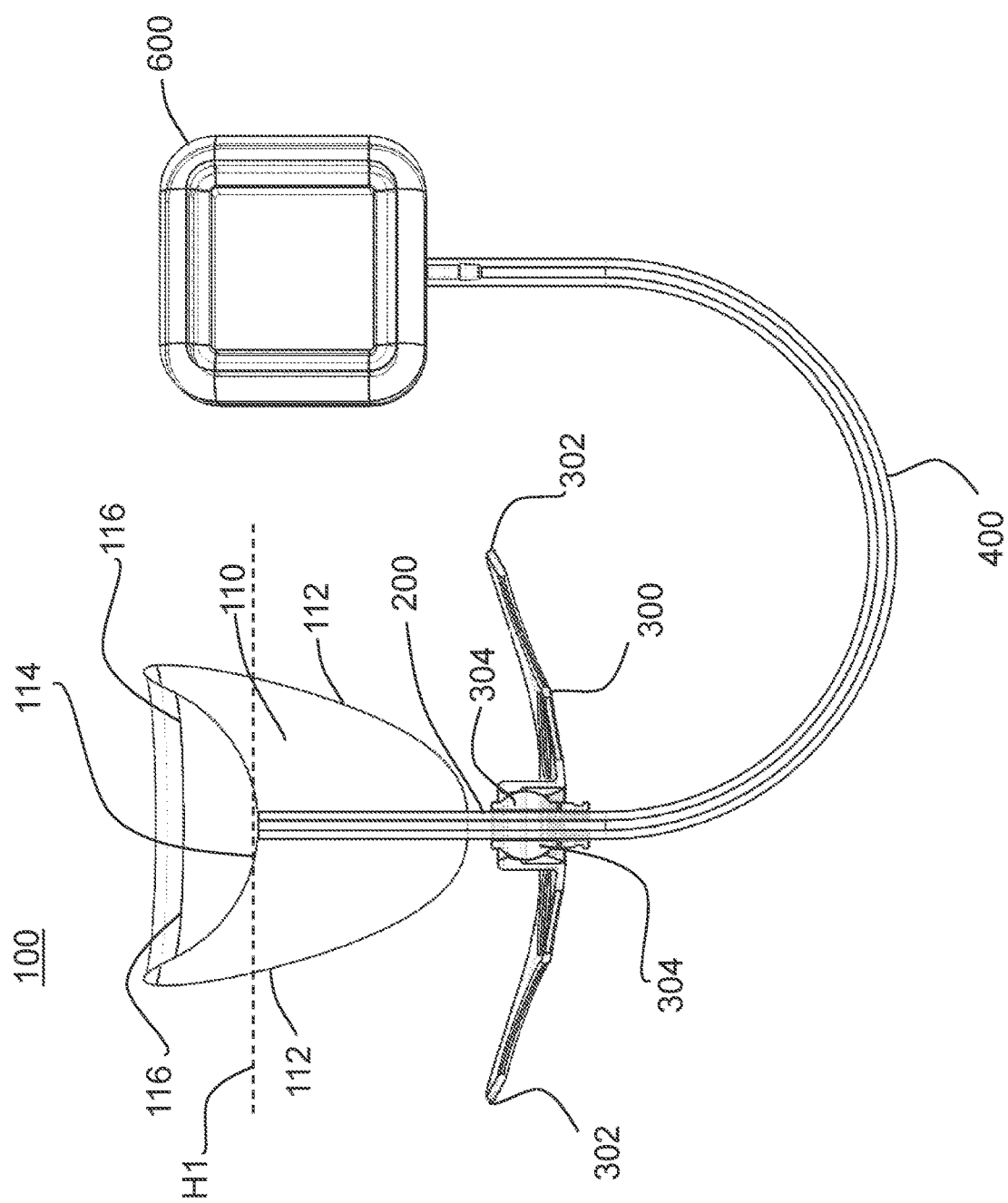
FIG. 3 illustrates the system in accordance with an exemplary embodiment of the disclosed subject matter.
Figure 8:
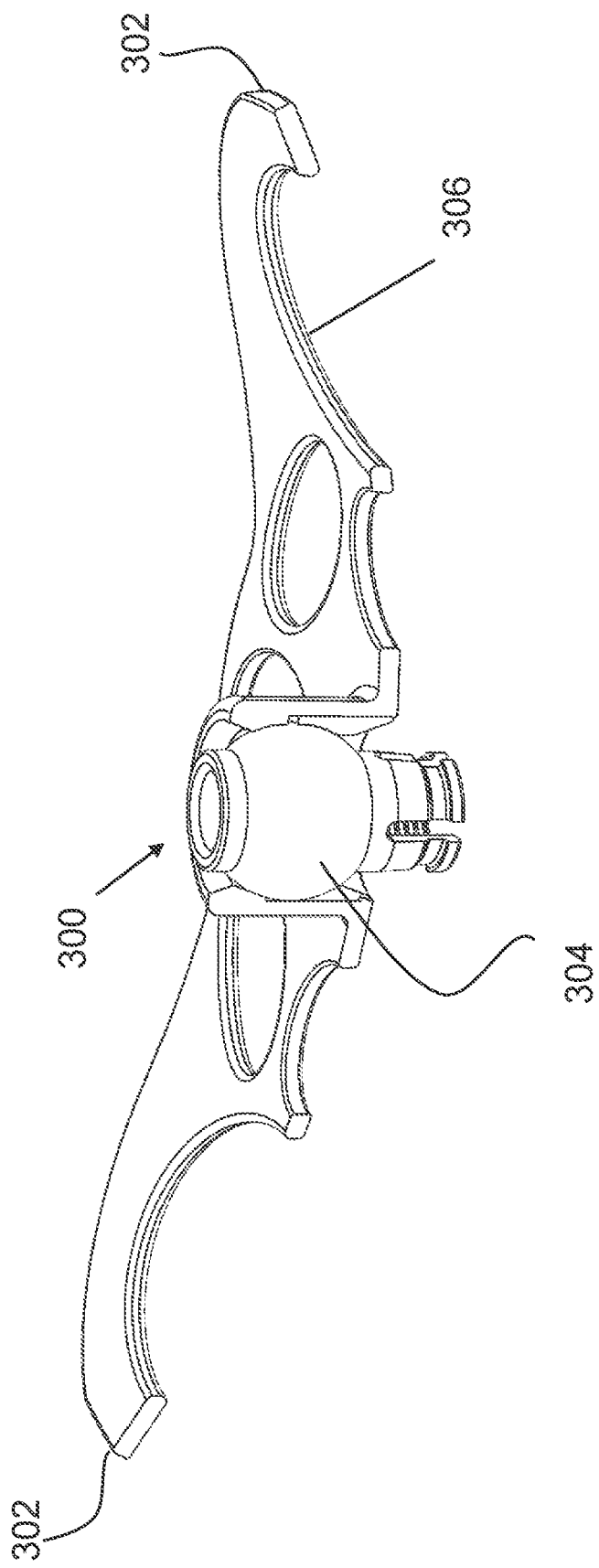
FIG. 8 is perspective view in partial cutaway of the therapeutic apical base of FIGS. 6-7 in accordance with exemplary embodiments of the disclosed subject matter.

One of the features of healthy heart function is proper physiological intracardiac flow. The atrioventricular pressure gradient is defined as the pressure difference (or a pressure differential) that produces or generates an energy and a force within the chambers of the heart that occurs naturally. As the pressure increases in the atrium and the pressure reduces in the ventricle, called the diastolic phase or diastole, blood flows from the higher pressure atrium into the lower pressure ventricle causing the valve leaflets to open and thus allowing the blood to pass through the valve orifice. During the systolic phase or systole, the pressure in the atrium is exceeded by the pressure in the ventricle thereby generating a pressure differential creating an energy and force which, in turn, pushes up and against the valve leaflets causing them to close and seal off the ventricle from the atrial chamber. The atrioventricular pressure gradient is the driving energy and force required to close the valve. During systolic ventricular contraction, the considerable forces of the atrioventricular pressure gradient are exerted on the closed atrial/ventricular valve. Very importantly, these forces are moved or transducted via the chordae tendinae and papillary muscles to and into the ventricular and septal walls. There is a resulting valvulo-ventricular wall interaction, which provides and enables the healthy ventricle to maintain structural integrity to maintain healthy the elliptical geometry, and provides functional support for blood ejection. During ventricular diastole, the ventricular pressure rapidly decreases. The valve opens and blood rushes from the atrium into the ventricle through the valve orifice. The valve leaflets function as a vector or steering mechanism, directing ventricular flow at an angle or vector to create vortical initial spin as illustrated in FIG. 1. Such angle or vector may be due to the asymmetry of the valve leaflets and/or to the different shapes and sizes of the leaflets. A vortex progression results. It is believed that the initial hemodynamic spin begins with inflowing blood, powered by the atrioventricular pressure gradient. On the ventricular side of the valve, the gradient pressure then engages that initial spin such that a vortex is created downstream. The resulting high velocity rotational flow, now a reservoir of kinetic energy within the ventricle is believed significant to proper blood flow velocity and volume through and out of the heart.

FIG. 2 illustrates that under certain conditions, such as a dilated cardiomyopathy (DCM) in which the heart becomes enlarged, the vortex fails to properly form, the elliptical shape is compromised or lost, the papillary muscles displaced resulting in the ventricle being unable to pump blood efficiently. Such conditions are marked by poor velocity, disturbed flow patterns, and poor cardiac output in which vortices are abnormal or absent and geometric distortion is present creating ventricular dysfunction.

In accordance with the disclosed subject matter, a flow vectoring and vortical intracardiac velocity offsetting balloon is implanted in the ventricular space of the heart. It is connected to a tether or shaft anchored at the apex. In one embodiment, the flow vectoring and vortical intracardiac velocity offsetting balloon is a fluid-filled adjustable balloon. The balloon may be contoured to the ventricular shape and may have a concave, convex, or other shape and sit within the ventricle either alone or as a component on the tether or shaft. The balloon is configured, shaped, sized, and fixed in place to raise the either the concave distal end or rounded distal end of said balloon into closer proximity of the atrio-ventricular valvular orifice, specifically the valvular leaflets, and the Left Ventricular Outflow Tract (LVOT) or Right Ventricular Outflow Tract (RVOT) in order to facilitate, enhance, and/or restore ventricular vortex and/or vortical hemodynamic flow. By implanting the flow vectoring vortical intracardiac velocity offsetting balloon, the normal blood vortex flow pattern that is disrupted by pathology or defect and healthy ventricular geometry may be assisted, enhanced, and/or restored. The hemodynamic velocity of inflowing blood may be altered by increasing or decreasing the distance of the balloon to the inflow tract of blood coming from the atrium into the ventricle by raising or lowering the 'member' or balloon.

Figure 11:
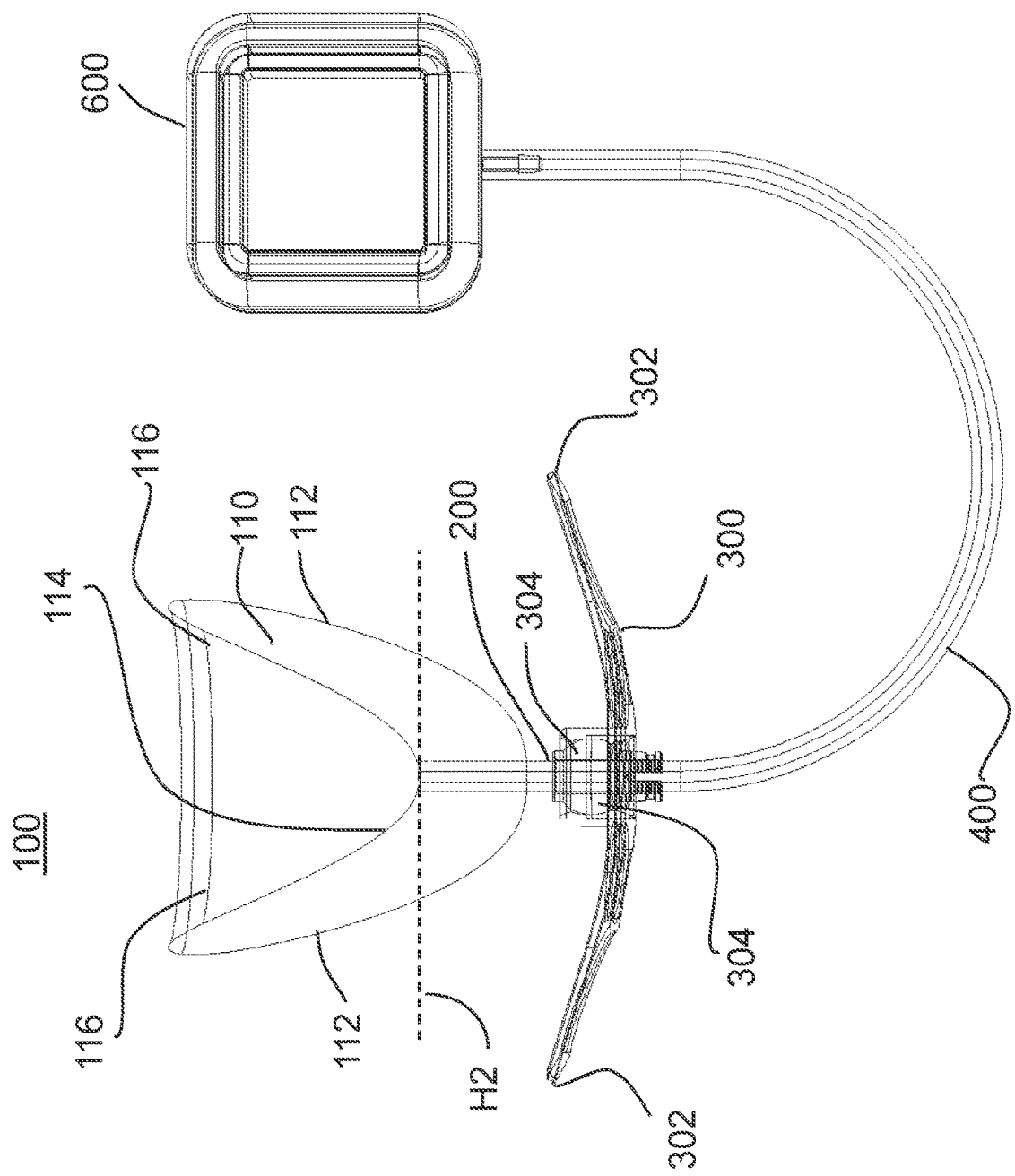
FIG. 11 illustrates the system of FIG. 3, with the balloon in a different orientation in accordance with an exemplary embodiment of the disclosed subject matter.

As illustrated in FIGS. 3 and 11, the implant device 100 includes a flow vectoring vortical intracardiac velocity offsetting balloon or 'offsetting balloon' which may be a fluid filled balloon 110 connected to a single or multi-lumen transducting conduit or shaft 200 (or force transducting tether). Balloon 110 is illustrated in a first configuration. The transducting shaft 200 is designed to be fixed to the apex A of the heart H by a therapeutic apical base plate assembly 300. (Implantation of the device 100 in the heart H is illustrated herein below in FIGS. 12 and 15.) The transducting conduit or shaft 200 is connected to a single or multi-lumen tube 400 after exiting the apex A. A single or multi-lumen tube 400 is connected to a control unit 600. Control unit 600 adjusts the device performance via a fluid communicating system when connected to the single or multi-lumen tube 400.

In some embodiments, the balloon 110 is fabricated with or covered, encapsulated, or patched with a material that inhibits thrombosis and/or promotes endothelialization and/or embolic free blood flow, e.g., but not limited to ePTFE, Dacron, or other materials. The material may be easily detachable from the balloon 110. Balloon 110 includes a proximal portion 112 having a surface that is contoured to approximate the shape of the heart's ventricle and a distal portion 114 having a surface and may have a concave or recessed shape, including a raised rim portion 116. The central portion of distal portion 114 defines position HI while in the first configuration. Balloon 110 is purposefully configured, shaped, sized, and fixed in place to raise the distal end 114 into closer proximity of the atrio-ventricular valvular apparatus and the atrial outflow tract/ventricular inflow tract in order to facilitate, enhance, and/or restore ventricular vortex and/or vortical hemodynamic flow by either accelerating or decelerating the outflow velocity of blood by occupying ventricular volume and shortening or lengthening the distance from the ventricular outflow tract. Hemodynamic upturn is created by the pressure gradient's driving force and shape as blood impacts and flows out of or off of of the vortical intracardiac velocity adjusting balloon. For example, the location HI and the upturned portions 116 of distal portion 114 provide desirable flow characteristics, as discussed herein.

As illustrated in FIGS. 3-6, balloon 110 is secured to the apex A of the patient's heart by therapeutic apical base plate assembly 300 including the base plate 302 and a ball jointed portion 304. In some embodiments, round oval cutouts 306 are defined in the base plate 302 to allow fibrous tissue in-growth for long term security.

Figure 9:
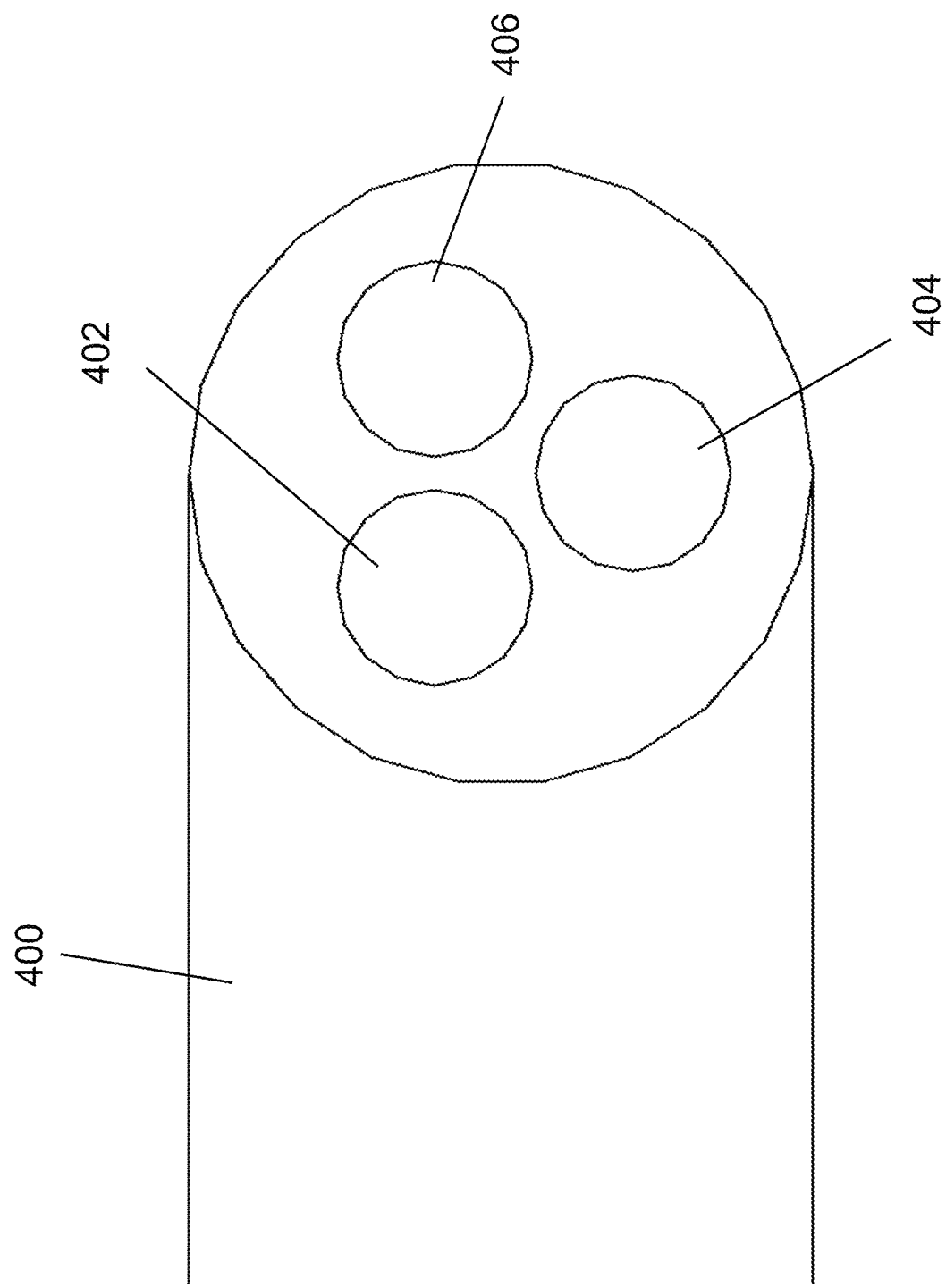
FIG. 9 is a view in partial section of the multi-lumen tube in accordance with exemplary embodiments of the disclosed subject matter.
Figure 10:
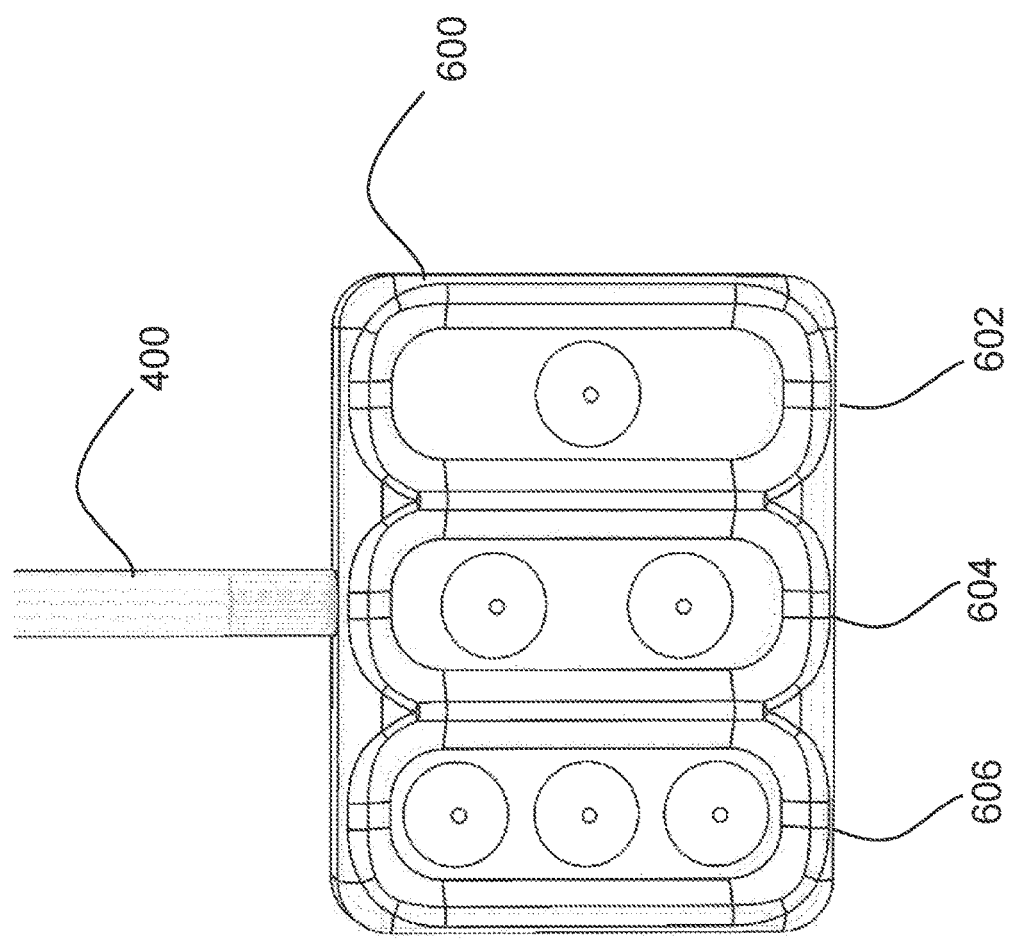
FIG. 10 is a view of the control unit in accordance with exemplary embodiments of the disclosed subject matter.
Figure 10A:
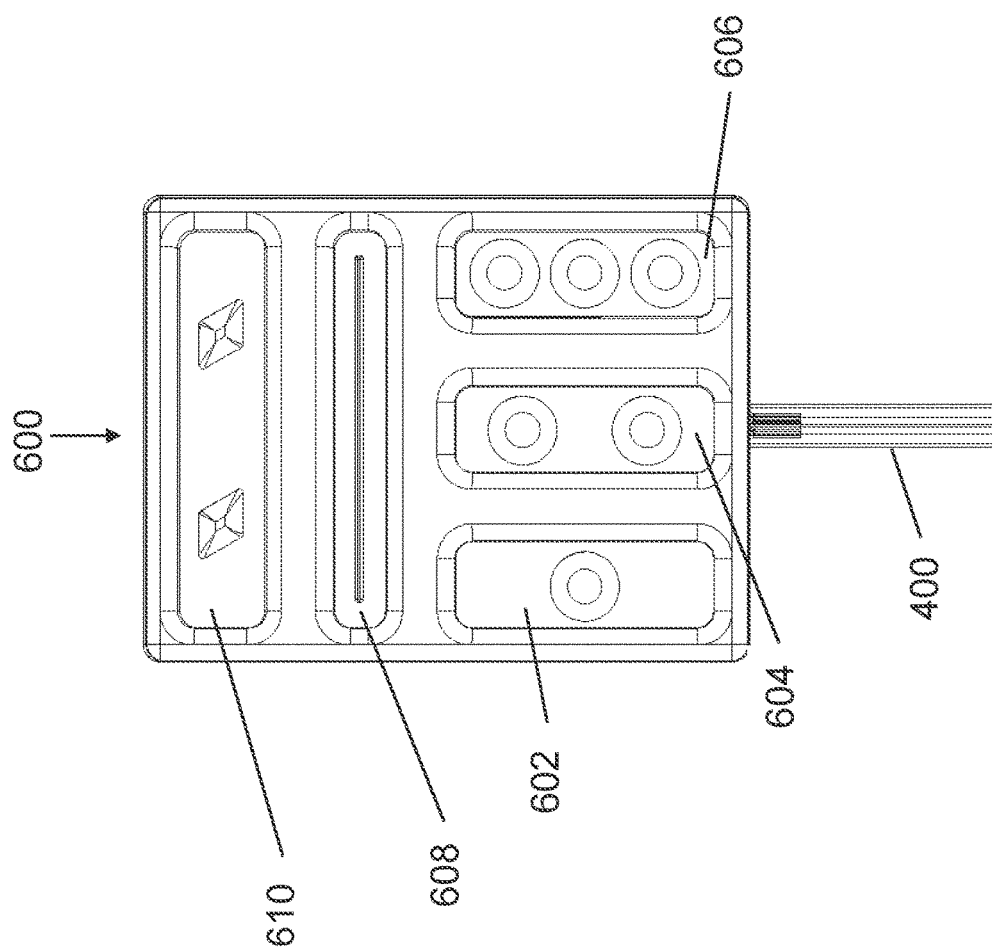
FIG. 10(A) is a view of the control unit in accordance with a further embodiment of the disclosed subject matter.

With reference to FIGS. 9-10, the control unit 600, which is implanted in the patient beneath the skin and capable of palpation by the surgeon, is provided to adjust the shape and size of the balloon 110. In some embodiments, control unit 600 is provided with three independent contained chambers 602, 604 and 606, each identifiable below the skin in some embodiments by palpable protrusions, one palpable protrusion for chamber one 602, two palpable protrusions for chamber two 604, and three palpable protrusions for chamber three 606. In another embodiment, control unit 600' is illustrated in FIG. 10(A) and includes five independent chambers, three as above 602', 604' and 606', with an additional two chambers 608' and 610' having a horizontal orientation and providing electrical, power source, and/or memory chambers to facilitate data acquisition from sensors within the balloon, the shaft, and or/the base plate. The control unit 600 is in fluid communication, via the tube 400 and shaft 200, with the balloon 110. As illustrated in FIG. 9, tube 400 includes a plurality of lumens 402, 404, and 406 in respective fluid communication with chambers 602, 604 and 606. As illustrated in FIG. 10, control unit 600 has a needle access pad of silicone and/or ePTFE, non-porous, or any semi-porous material, to allow fibrous tissue ingrowth (the body's method of preventing infection and facilitating hemostasis). In some embodiments, fluid is introduced to or removed from chambers 602, 604 and 606 to adjust the shape and/or location of balloon 110. In chamber 602, fluid is introduced or removed to increase or decrease the size of balloon 110 generally, and in particular the shape of the distal portion 114 for directing ventricular flow. With reference to FIG. 3, the distal portion 114 defines a position H1 with a relatively shallow concave depression when balloon 110 is in the first configuration. FIG. 11 illustrates balloon 110 in a second configuration, in which distal portion 114 defines a position H2 with a deep concave depression. Typically, the balloon 110 includes less fluid in the second configuration than in the first configuration. Other lumens may be used for hydraulic axial adjustment, communication of sensor data with the control unit, wiring, data storage, and power delivery, etc. The control unit 600 may contain power sources, sensoring control modules, the sensors themselves, and/or communications units.

Figure 12:
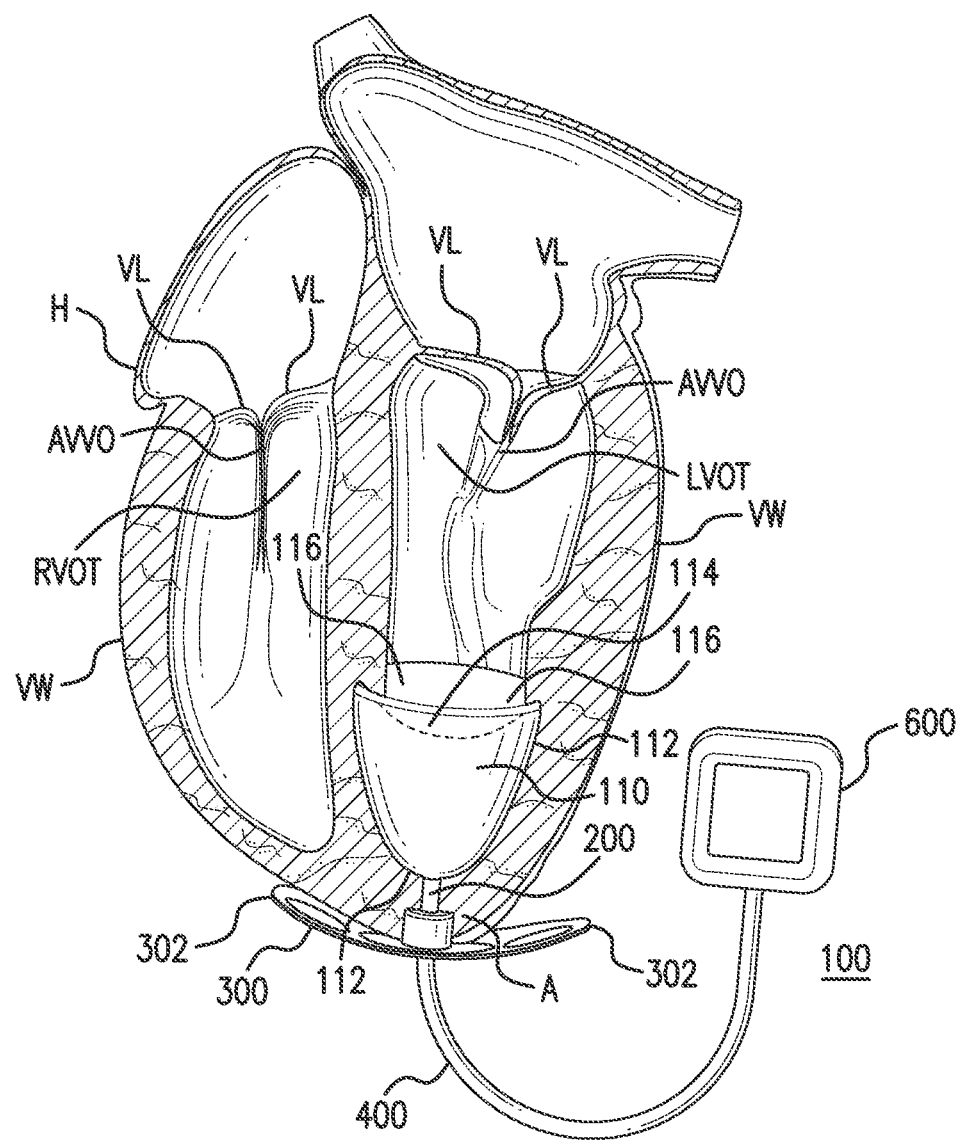
FIG. 12 illustrates the system of FIG. 3 installed in the human heart in accordance with an exemplary embodiment of the disclosed subject matter.

As illustrated in FIG. 12, the proximal portion 112 of balloon 110 is contoured to the shape of the heart's ventricle VW, the distal portion 114 is concave and purposefully configured, shaped, sized, and fixed in place to raise the concave distal end 114 of balloon 110 into closer proximity of the atrio-ventricular valvular orifice AVVO, specifically the valvular leaflets VL, and the Left Ventricular Outflow Tract LVOT or Right Ventricular Outflow Tract RVOT in order to facilitate, enhance, and/or restore ventricular vortex and/or vortical hemodynamic flow by accelerating or decelerating the blood flow.

The distal concave end 114 of the balloon 110, closest to the valvular orifice AVVO and in the path of the LVOT or RVOT, receives the ventricular inflow blood, changing its velocity with surface contact in the distal concave shape 114, and proximity, in such a manner that the impact of said blood onto the distal end of the balloon 110 makes an upturn at rim portion 116, at the proper distance from the leaflet, by impacting the concave shape, and the native hemodynamic outflow force being sufficient to initiate the hemodynamic upturn required, thereby allowing the native atrioventricular pressure gradient to properly effect and impact the formation of proper ventricular vortex/vortices. The proximity of the distal end 114 of the balloon 110 to the valvular orifice AVVO and the LVOT or RVOT is spatial and such that the velocity may be changed by surface contact and/or proximity and the hemodynamic upturn may occur.

In some embodiments, the proximal end 112 of the balloon 110 is configured to aid and/or restore the proper healthy elliptical shape of the intracardiac ventricle and acts a 'mold' to assist in positive geometric remodeling of the ventricular free wall VW and has an outer surface 112 in firm contact with the endocardium. In some embodiments, the balloon is shape compliant to form to any shape within the atrium, the ventricle, or other existing spaces to include the apical endocardium or the left atrial appendage. In some embodiments, the balloon is asymmetric or symmetric.

In some embodiments, the implant system includes sensoring nodes, transducers, or other diagnostic surveillance equipment that transmit information to an external receiving platform.

Figure 13:
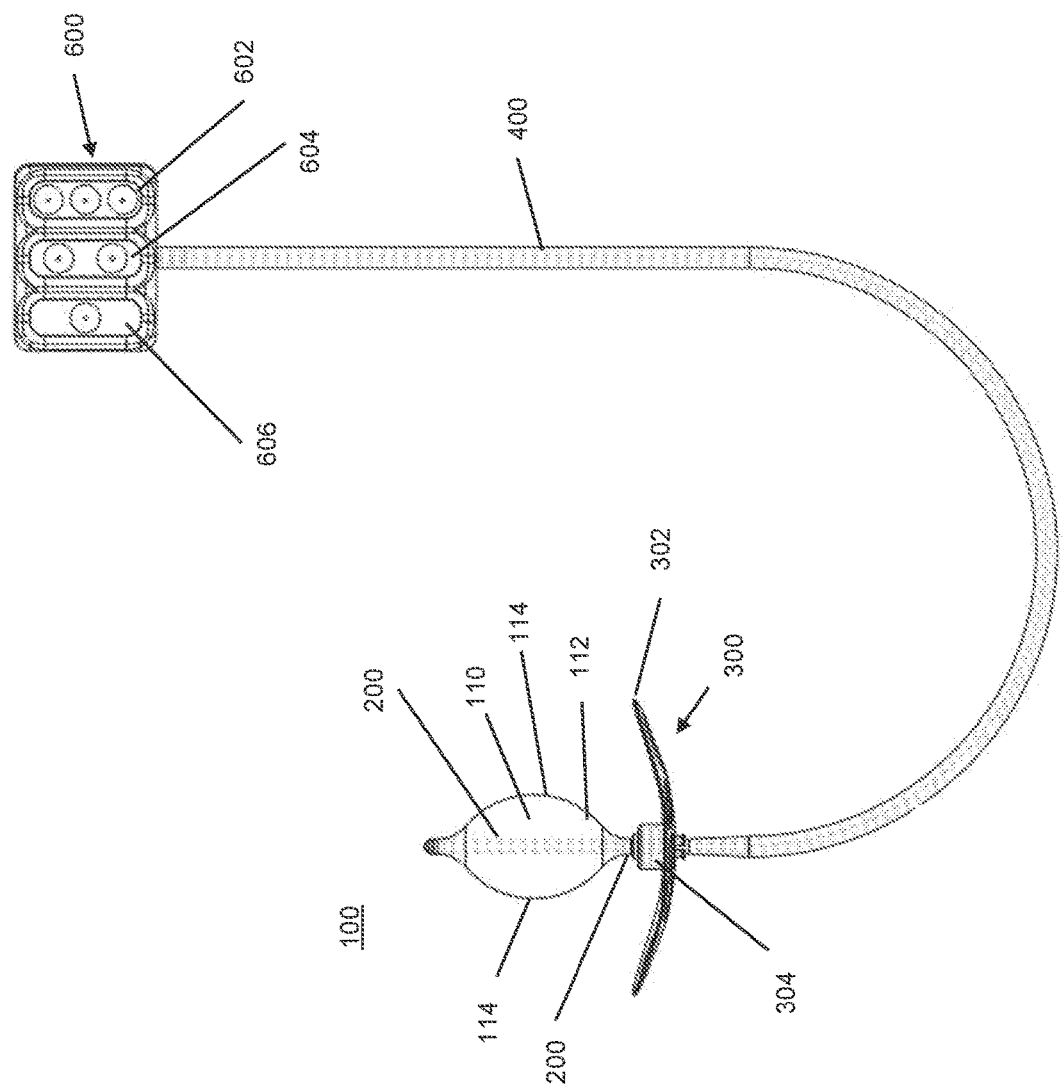
FIG. 13 illustrates a system accordance with another exemplary embodiment of the disclosed subject matter.
Figure 14:
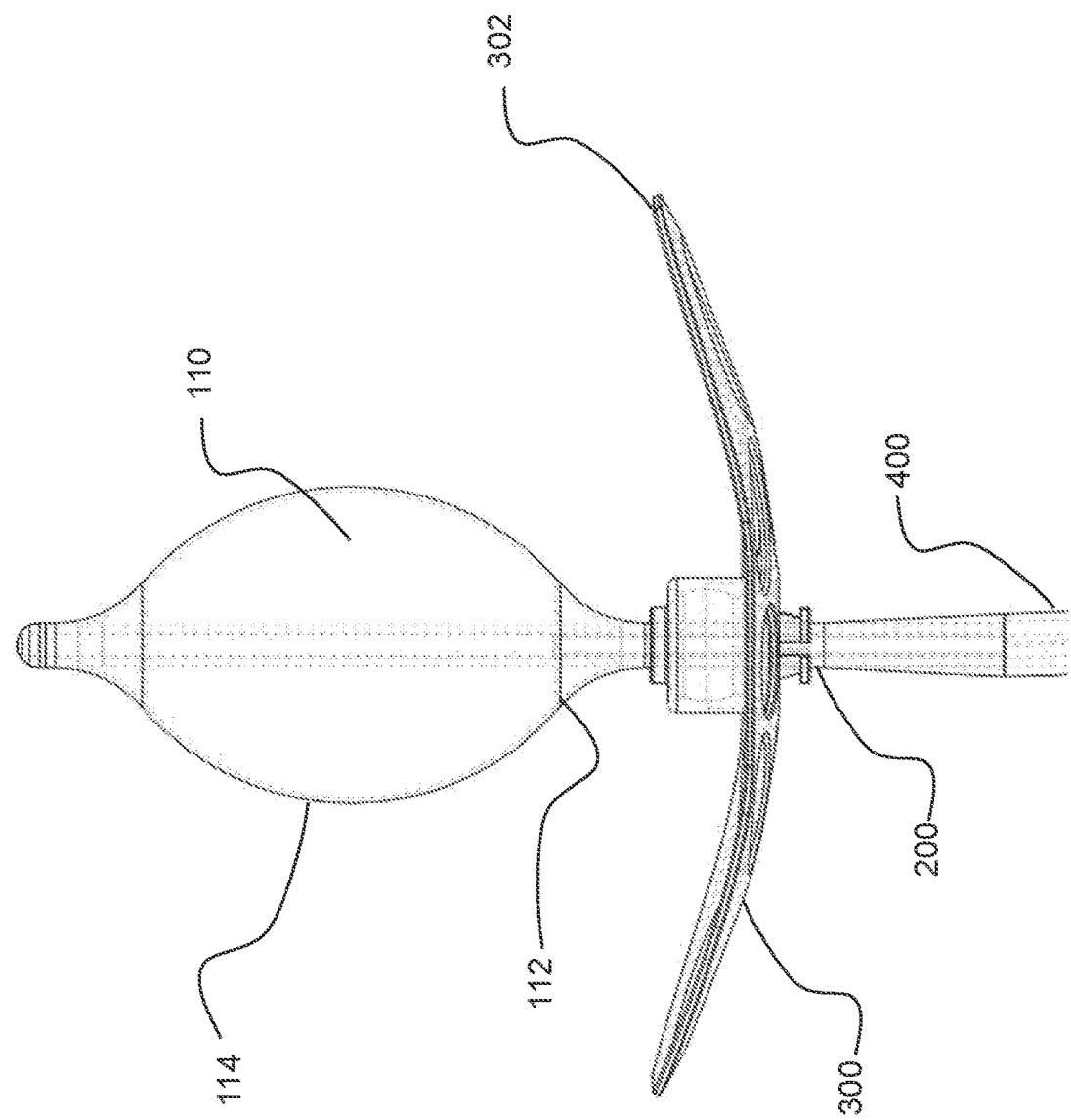
FIG. 14 is an enlarged view of a portion of the system of FIG. 13 in accordance with an exemplary embodiment of the disclosed subject matter.
Figure 15:
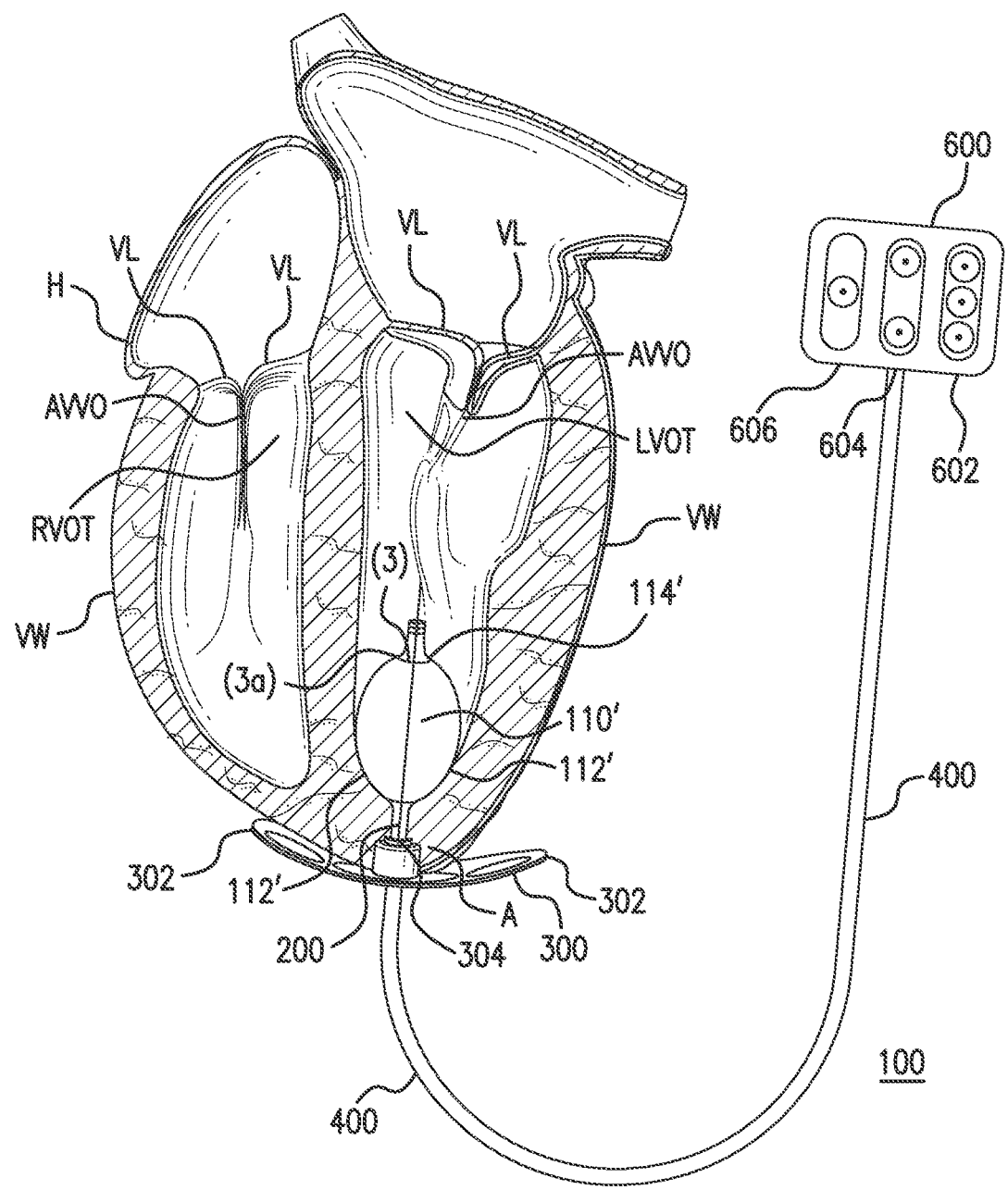
FIG. 15 illustrates the system of FIG. 13 installed in the human heart in accordance with an exemplary embodiment of the disclosed subject matter.

FIGS. 13-15 illustrate another embodiment of the implant device 100'. Implant device 100' is substantially identical to the device of implant device 100, with the difference noted herein. In particular, implant device 100' includes balloon 110' having a convex proximal portion 112' which conforms to the ventricular wall. Balloon 110' further defines a convex 3 distal portion 3a 114'. Balloon 110' purposefully configured, shaped, sized, and fixed in place to raise the convex distal end 114' of balloon 110' into closer proximity of the atrio-ventricular valvular orifice AVVO, specifically the valvular leaflets VL, and the Left Ventricular Outflow Tract LVOT or Right Ventricular Outflow Tract RVOT in order to accelerate or decelerate hemodynamic velocity and volume, facilitate, enhance, and/or restore ventricular vortex and/or vortical hemodynamic flow.

The balloon enhances, facilitates, and/or restores a diastolic vortex formation at a spatial point at which inflow velocity is changed and hemodynamic upturn is detected. The balloon provides a velocity change surface for diastolic blood inflow. The balloon provides a surface to change diastolic blood inflow vector. The balloon provides a distal diastolic vortex-facilitating surface.

In some embodiments, the balloon is adjustable in volume, size and shape at any time, to be constantly adjustable so that the distal diastolic vortex-facilitating surface may conform to patient specific anatomy and meet the specific individual need of each individual patient as hemodynamic flow conditions change or to assist in changing the flows.

The balloon facilitates vortical blood formation during diastole. The balloon reduces hemodynamic ventricular volume and/or changes ventricular velocity and eliminates stagnant or pooled blood mainly in the apical regions of the ventricle.

The adjustability of the balloon in volume, size and shape provides reduction of ventricular volume that conforms to patient-specific anatomy and meets the specific individual need of each individual patient.

The shaft/conduit acts to transduct or transfer native cardiac energy and force to the ventricular free wall via the therapeutic apical anchoring base plate.

The balloon acts to capture cardiac muscular and/or rotational and force and facilitates itself as a conduit for transfer of said energy and force to the therapeutic apical anchoring base plate via transduction utilizing the shaft it is connected to as the conduit.

The balloon acts to increase or decrease the ventricular volume, being an attached device or component within the ventricle, as it inflates or deflates.

The balloon acts to assist ventricular systole or diastole, being an attached device or component within the ventricle powered either by the native heart or an internal or external power source and/or sources as it inflates or deflates.

The balloon acts to assist ventricular systole or diastole, being in fluid contact with the another balloon in different chamber of the heart using the pressure differential as a driving force or power source as it inflates or deflates.

The balloon configuration can include a "balloon within a balloon," which can be adjusted by changing the volume of the reservoir to move the shaft axially or longitudinally (up & down) in extension or retraction inside a human heart.

The shape of the balloon (concave and/or another shape) can change hemodynamic velocity with contact, vector hemodynamic upturn, and engage the burst of pressure native to the atrioventricular pressure gradient to facilitate, enhance, and/or restore vortex, vortical flow, and/or ventricular flow in a ventricle in a human heart.

The balloon on a shaft/conduit can be moved and/or fixed, spatially near a native or prosthetic structure, component, or the native ventricular outflow tract in, above, or below a valve orifice, to effect the velocity, vector, and/or hemodynamic upturn of flow off of the native or prosthetic valve leaflets to effect, enhance, and/or restore or repair vortex, vortical flow, and/or ventricular flow.

In some embodiments, the therapeutic apical base plate includes a ball-joint and can be implanted at a bias to move a structure, component, or device in, above, or below a valve orifice or between valve leaflet to effect, change, and/or repair native vortex and/or vortical and/or ventricular flow as deployed to assist a native or prosthetic structure, a native or prosthetic component, or prosthetic device.

It will be appreciated that the methods and systems described above are set forth by way of example and not of limitation. Numerous variations, additions, omissions, and other modifications will be apparent to one of ordinary skill in the art. Thus, while particular embodiments have been shown and described, it will be apparent to those skilled in the art that various changes and modifications in form and details may be made therein without departing from the spirit and scope of this disclosure and are intended to form a part of the disclosure as defined by the following claims, which are to be interpreted in the broadest sense allowable by law.

What is claimed is:

1. An implant system for improving intracardiac blood flow, the implant system comprising:
    a shaft comprising a proximal end, a distal end, and a conduit therethrough;
    a flow-vectoring inflatable balloon comprising a semi-ellipsoid shape extending from a proximal portion having a first cross-sectional area to a distal portion having a second cross-sectional area that is larger than the first cross-sectional area, the distal portion coupled to a distal end of the shaft and the proximal portion coupled to the shaft proximal to the distal end, wherein the distal portion comprises:
        a top rim defining a distal-most circumference of the distal portion; and
        a top surface extending within an area defined by the top rim, the top surface being upturned at the top rim and having a concave-up shape extending towards the proximal portion, wherein, upon inflation or deflation of the balloon, the shaft moves longitudinally relative to the proximal portion of the balloon;
    an adjustment assembly coupled between the distal end and the proximal end of the shaft, the adjustment assembly proximal to the flow-vectoring inflatable balloon; and
    an apical base plate coupled to the adjustment assembly;
    wherein the adjustment assembly comprises:
        a joint portion comprising a ball joint coupled between the shaft and the apical base plate, wherein the joint portion is configured to adjust an angle of the apical base plate relative to the shaft.

2. The implant system of claim 1, further comprising:
    a tube comprising a plurality of lumens, a proximal end, and a distal end, the tube coupled proximal to the distal end to the apical base plate assembly; and
    a control unit coupled to the proximal end of the tube and in fluid communication with the plurality of lumens; and
    a fluid disposed within the inflatable balloon, the shaft, the tube, and the control unit.

3. The implant system of claim 2, wherein the fluid is selected from the group consisting of: a gas, a liquid, and a gel.

4. The implant system of claim 1, wherein the flow-vectoring inflatable balloon comprises a polymer.

5. The implant system of claim 4, wherein the polymer comprises ePTFE or Dacron.

6. The implant system of claim 1, wherein the top surface comprises a first height between the top surface and the proximal portion in a first configuration and a second height between the top surface and the proximal portion in a second configuration that is larger than the first height.

7. The implant system of claim 6, wherein the inflatable balloon has a first fill volume in the first configuration and a second fill volume in the second configuration that is smaller than the first volume.

8. The implant system of claim 6, wherein the top surface further comprises a third configuration, the third configuration having a third fill volume that is larger than the first fill volume configured to invert the concave shape of the top surface to a convex shape.

9. The implant system of claim 1, wherein the shaft comprises an axial adjustment lumen for adjusting the axial position of the inflatable balloon.

10. The implant system of claim 1, wherein the semi-ellipsoid shape substantially conforms to a shape of a chamber of a heart.

11. The implant system of claim 1, wherein the ball joint member comprises a shaft retention feature.

12. The implant system of claim 1, wherein the apical base plate comprises a plurality of cutouts configured to allow fibrous tissue in-growth.

13. The implant system of claim 1, wherein the apical base plate comprises an inflatable structure.

14. The implant system of claim 1, wherein the apical base plate comprises an expandable structure.

15. The implant system of claim 1, further comprising a sensor coupled to the shaft.

16. The implant system of claim 1, wherein the inflatable balloon is a first inflatable balloon comprising a second inflatable balloon disposed therein.

17. The implant system of claim 1, wherein the control unit comprises a plurality of access sites.

18. The implant system of claim 1, wherein the control unit comprises a plurality of fluid reservoirs.

19. The implant system of claim 1, wherein the shaft does not extend beyond the top surface having the concave-up shape.

* * * * *